United States Patent [19]

Oroshnik

[11] 4,064,183

[45] Dec. 20, 1977

[54] SYNTHESIS OF VITAMIN A, INTERMEDIATES AND CONVERSION THEREOF TO VITAMIN A

[75] Inventor: William Oroshnik, Plainfield, N.J.

[73] Assignee: SCM Corporation, New York, N.Y.

[21] Appl. No.: 662,333

[22] Filed: Mar. 1, 1976

Related U.S. Application Data

[60] Division of Ser. No. 566,981, April 10, 1975, Pat. No. 4,035,425, which is a division of Ser. No. 353,215, April 23, 1973, Pat. No. 3,949,006, which is a continuation-in-part of Ser. No. 246,939, April 24, 1972, abandoned.

[51] Int. Cl.$^2$ .............................................. C07C 29/00
[52] U.S. Cl. ................................... 260/617 A; 560/260
[58] Field of Search ........................ 260/617 A, 488 A

[56] References Cited

U.S. PATENT DOCUMENTS

| | | | |
|---|---|---|---|
| 2,452,386 | 10/1948 | Milas | 260/617 A |
| 2,586,305 | 2/1952 | Copenharen | 260/617 A |
| 2,602,092 | 7/1952 | Oroshnik | 260/617 A |
| 2,842,600 | 7/1958 | Oroshnik et al. | 260/617 A |
| 2,845,462 | 7/1958 | Oroshnik | 260/617 A |
| 2,920,103 | 1/1960 | Oroshnik | 260/617 A |
| 3,006,968 | 10/1961 | Pasedach et al. | 260/617 A |

*Primary Examiner*—Bernard Helfin
*Assistant Examiner*—James H. Reamer
*Attorney, Agent, or Firm*—Richard H. Thomas

[57] ABSTRACT

A synthesis of novel Vitamin A intermediates from beta-ionone is described as well as a conversion of the intermediates to Vitamin A. The length of the conjugated aliphatic side chain of beta-ionone is increased while still ultimately obtaining the desired trans form of Vitamin A. In general, beta-ionone is ethynylated to ethynyl-beta-ionol, the hydroxyl of which is etherified to form an ethynyl-terminated, alkoxy-substituted, beta-ionol intermediate. The intermediate is coupled through its copper derivative with a compound like chloro-isopentenyl acetate to produce a $C_{20}$ skeleton. By semi-hydrogenation, the acetylenic bond on the $C_{20}$ skeleton is converted to an ethylenic bond, and by hydrolysis the terminal ester moiety is converted to a hydroxyl group. Treatment with a strong base removes the alkoxy group to produce Vitamin A.

2 Claims, No Drawings

SYNTHESIS OF VITAMIN A, INTERMEDIATES AND CONVERSION THEREOF TO VITAMIN A

This is a division of application Ser. No. 566,981, filed April 10, 1975, now U.S. Pat. No. 4,035,425, which in turn is a division of application Ser. No. 353,215, now U.S. Pat. No. 3,949,006 filed April 23, 1973. The latter is a continuation-in-part of application Ser. No. 246,939, filed April 24, 1972 now abandoned.

Vitamin A is a known organic substance which is essential for growth and for maintaining animal life but which cannot be synthesized by the animal nor provide energy by itself. Because of its importance, numerous attempts have been made to synthesize Vitamin A. In 1947 Hoffman-LaRoche reported the first successful laboratory synthesis of Vitamin A, marking the culmination of what had been a formidable scientific and economic challenge to the organic chemist for several decades. Since that time a number of different syntheses of Vitamin A have been suggested but most are not considered commercially feasible.

Vitamin A is generally considered to have this formula:

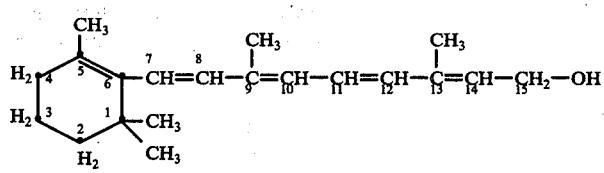

It is important to distinguish between the cis and trans forms of Vitamin A. The trans form has much higher biological activity than any of the possible cis forms. Likewise, compounds of the above formula in which all double bonds are shifted one carbon atom to the left are only very slightly active.

With few exceptions, all syntheses of Vitamin A utilize beta-ionone as the starting material. Its ready availability and the fact that, structurally, it represents about 65 percent of the desired Vitamin A molecule, as illustrated by its following formula, make it a logical starting point.

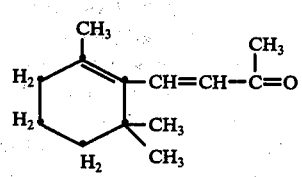

In spite of this advantage, the subtleties involved in extending the beta-ionone side chain to Vitamin A frustrated the efforts of numerous chemists for many years. One major difficulty with the use of beta-ionone as the starting material in the synthesis of Vitamin A is the behavior of the beta-ionol group on dehydration. Normally, the extension of an alpha, beta unsaturated ketone to a longer conjugated polyene is accomplished through nucleophilic addition to the carbonyl group, that is, Grignard reactions, Reformatsky reactions, ethynylations, Knoevenagel reactions, etc., resulting in a carbinol containing the desired attached group. The carbinol is then dehydrated to evolve the additional ethylenic bond linking the two groups. Thus, in the case of beta-ionols, this should produce the beta-ionylidene group bringing the molecule one step closer to Vitamin A, or:

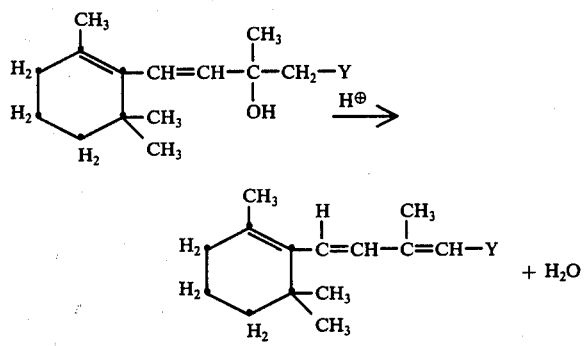

in which Y is defined as alkenyl or alkynyl, either of which can be substituted or unsubstituted.

Unfortunately, except in special cases, dehydration of beta-ionols does not proceed in this direction but rather in the opposite direction to produce the retroionylidene group.

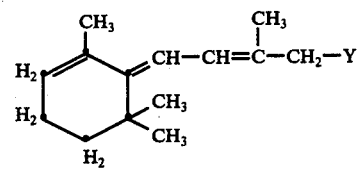

This went unrecognized for many years until the early 1950's. As a result, many workers wrongly assigned beta-ionylidene structures to what were actually retroinylidene structures and the literature on Vitamin A synthesis at that time was confused.

The retroinonylidene structure is more thermodynamically stable than the beta-ionylidene which is sterically hindered at the ring side chain junction. Beta-ionols, and vinylogues thereof, always dehydrate to retroionylidenes, unless the designated Y group contains a sufficiently strong electron-attracting group, such as —C≡N, —COCl, —CHO, or —C≡C—.

Although the Roche synthesis was evolved before these facts were known, it fortuitously avoided the above pitfall in dealing with intermediates which were not beta-ionols. On the other hand, the known Philips and Eastman synthesis do involve beta-ionol intermediates. However, in order to avoid retroinoylidene formation, the Philips process utilizes the —C≡N group, and the Eastman process employs the —CHO group. In both of these processes, the price for these safety factors is high. The final products, the Vitamin A nitrile and Vitamin A aldehyde, have to be reconverted to Vitamin A via expensive lithium aluminum hydride reactions. The more recent BASF process, German Pat. No. 957,942, utilizes the Wittig reaction for extending the beta-ionol side chain and thus avoids the troublesome beta-ionol complications. The Wittig reaction, however, tends to be costly.

In short, the past 20 years of effort in this field has established two key factors for providing a commercially practical synthesis of Vitamin A:
1. The cost of building the $C_{20}$ skeleton.
2. The specificity of the chemistry involved in passing from the $C_{20}$ intermediate to Vitamin A.

The present process provides a relatively inexpensive synthesis for forming an intermediate having a $C_{20}$ skeleton, particularly useful for the synthesis of Vitamin A, and one that embodies a chemical route free of ambiguities for conversion of the $C_{20}$ intermediate to Vitamin A. The synthesis starts with beta-ionone and forms several novel beta-ionol intermediates while avoiding formation of retroisomers as well as minimizing formation of the cia forms of Vitamin A.

In general, beta-ionone is ethynylated to ethynylbeta-ionol. The hydroxyl of the alcohol is then etherified to form an ethynyl-terminated, alkoxy-substituted, beta-ionyl intermediate. The intermediate is coupled as by the acetylenic copper derivative with a compound like chloro-isopentenyl acetate (1-chloro-4-acetoxy-2-methyl-2-butene) to produce a $C_{20}$ skeleton. The acetylenic bond on the $C_{20}$ skeleton is converted by semi-hydrogenation to an ethylenic bond, and the terminal ester moiety is converted by hydrolysis to a hydroxyl group.

The intermediate $C_{20}$ skeleton at this juncture of the process has two isolated double bonds separated by a methylene group.

It is well recognized that a methylene group situated between two double bonds represents a very reactive prototropic center. In the above $C_{20}$ skeleton, strong bases would, therefore, be normally expected to remove a proton (H+) from carbon-12 to give a carbanion and result, upon neutralization, in the conjugation of the two double bonds adjacent to it. However, it was found instead, that after formation of a carbanion at $C_{12}$ in the above compound, with sufficiently strong bases, the alkoxy group was eliminated at carbon-9 to give an additional double bond. Thus, a 1,4-elimination of alcohol was effected rather than simply isomerization of the double bonds present. The formation of the additional double bond results in conjugation of all five double bonds in the molecule to give Vitamin A.

A general description of the process and novel intermediates is intially given followed by specific examples of various steps of the process. For convenience of reference Roman numerals appearing to the left of structural formulas are similarly used in the claims to represent the same formulas.

Beta-ionone as the starting material is reacted with a metal acetylide, such as lithium or sodium acetylide, in a known manner to provide a compound having a terminal acetylene group and a hydroxyl group on the adjacent carbon atom, that is, the compound 5-(2,6,6-trimethylcyclohexen-1-yl)-3-methyl-pent-4-en-1-yn-3-ol (ethynyl-beta-ionol), as represented by the following formula:

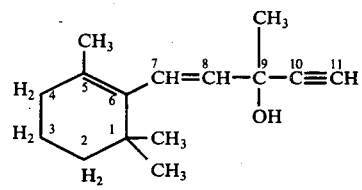

(Numbered in accordance with IUPAC carotenoid numbering system)

A method of ethynylating beta-ionone is described in an article by W. Oroshnik and A. D. Mebane published in J.A.C.S., 71, 2062 (1949).

The ethynyl beta-ionol is next etherified at the hydroxyl group. The process involves stirring the ethynyl beta-ionol with a dialkyl sulfate, such as diethyl sulfate, in an aprotic solvent such as dimethyl formamide in the presence of a base such as sodium hydroxide, barium hydroxide or sodium carbonate at room temperature for several hours. Dimethyl sulfoxide may also be used as the reaction medium. Dimethyl formamide is readily recovered by distillation of the reaction mixture under moderate vacuum. Dimethyl formamide recoveries of at least 70 percent have been obtained without difficulty. A class of compounds is obtained having the following general formula:

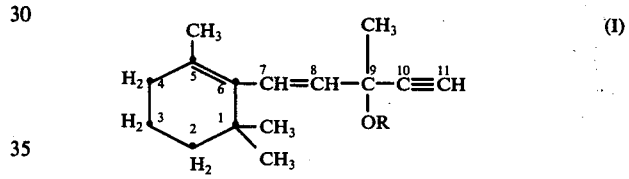

in which R is lower alkyl or alkenyl, such as up to 5 carbon atoms, preferably methyl or ethyl, phenyl or aralkyl up to 10 carbon atoms. An example of a compound of this class, using normal organic nomenclature, is ethyl 1-ethynyl-1-methyl-3-(2,6,6-trimethyl-1-cyclohexen-1-yl)allyl ether.

A compound of Formula I is coupled with another reactant to form a basic $C_{20}$ skeleton of Vitamin A. Such other reactant may be the acetoxy analogue of the chloroester of the added chain length required, for example, the aforementioned chloro-isopentenyl acetate. The chloroacetate is known and prepared by the chlorohydrination of isoprene in glacial acetic acid, as described in an article by W. Oroshnik and R. A. Mallory, J.A.C.S., 72, 4608 (1950).

The coupling reaction is accomplished through a preformed cuprous acetylenyl derivative. Coupling with a chloroester may not be carried out with a copper-catalyzed Grignard reaction because of the reactivity of the Grignard reagent toward the acetate group in the chloro-acetate reactant. Organo copper compounds are inert toward esters. The cuprous salts of substituted acetylenes, unlike cuprous acetylide, have been found to be non-explosive and quite stable even at elevated temperatures.

The coupling reaction involves pre-forming a cuprous salt of the compound of Formula I and reacting the cuprous salt with the coupling reactant in an aprotic solvent, such as dimethyl formamide. The coupling reactant may have the following formula:

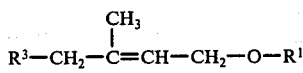

in which R¹ is hydrogen or

R² being a lower alkyl up to 5 carbon atoms, phenyl, substituted phenyl up to 10 carbon atoms or an aralkyl up to 10 carbon atoms; and R³ is a halogen. The coupling reaction results in a class of compounds having the following general formula:

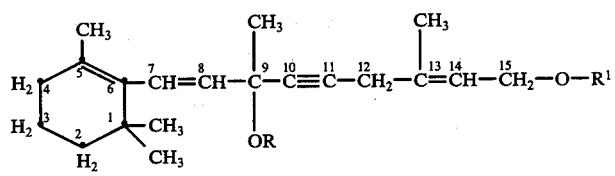

in which R and R¹ are as previously defined. An example of a compound of the class of Formula III, using carotenoid nomenclature based on the parent compound retinol, is: 10,11-didehydro-9-ethoxy-9,12-dihydroretinol acetate. Optionally, the coupling may be carried out by pre-forming the cuprous derivatives in situ through a Grignard intermediate in ether as well as in hexamethyl phosphoric triamide as the aprotic solvent.

A compound of Formula III is next subjected to a semi-hydrogenation to convert the acetylenic bond to an ethylenic bond, for example, by catalytic means. Lindlar catalyst (5 percent palladium on calcium carbonate modified by addition of lead) may be used, or Raney nickel may be used as the catalyst, treated with zinc acetate and a secondary amine, such as diethanolamine. The latter catalyst is referred to in an article by W. Groshnik, G. Karmas and A. D. Mebane, J.A.C.S., 74, 295 (1952). The semi-hydrogenation produces a class of compounds having the following general formula:

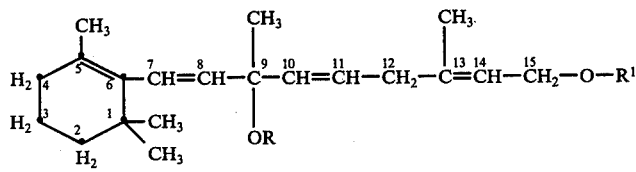

in which R and R¹ have the same meanings as previously given. An example of a compound of this class, using carotenoid nomenclature, is 9-ethoxy-9,12-dihydroretinol acetate.

As indicated, the terminal group R¹ of the compounds of Formulas III and IV can comprise a number of different groups such as hydrogen, acyl (COR²) in which the alkyl group contains up to about 5 carbon atoms, or phenacyl and substituted phenacyl with up to about 10 carbon atoms, or aralkyl acryl in which the aralkyl group contains up to about 10 carbon atoms. However, the terminal OR¹ group preferably is hydroxyl to obtain Vitamin A. This is accomplished by hydrolyzing the terminal group or otherwise converting the terminal OR¹ group to hydroxyl to form a class of compounds having the general formula:

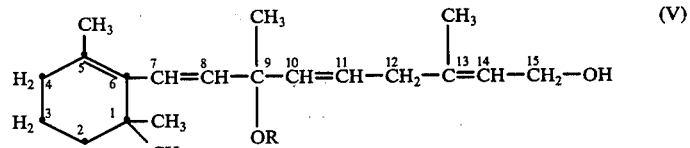

in which R has the same meaning as before. The hydrolysis or other treatment of the terminal group may occur at any desired time and need not follow the sequence herein given, that is after the semi-hydrogenation.

The intermediate compound of Formula V is an alkoxy substituted 9,12-dihydroretinol. This compound has two isolated double bonds separated by a methylene group (carbon-12). It is well recognized that a methylene group situated between two double bonds represents a very reactive prototropic center. In the above compound, strong bases would therefor normally be expected to remove a proton (H⁺) from carbon-12 to give a carbanion and result, upon neutralization, in the conjugation of two double bonds adjacent to it. However, it was found, contrary to expectations that, after formation of a carbanion at $C_{12}$ in the above compound, with sufficiently strong bases, the alkoxy group was eliminated at carbon-9 to give an additional double bond. Thus, a 1,4-elimination of alcohol (ROH) was effected rather than simply isomerization of the double bonds present. The formation of the additional double bond results in conjugation of all five double bonds in the molecule to give Vitamin A. This rearrangement and 1,4-elimination of ROH may be illustrated as follows:

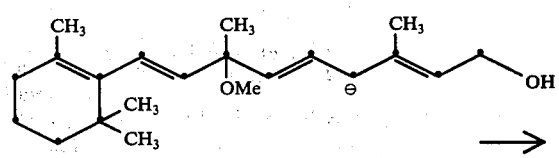

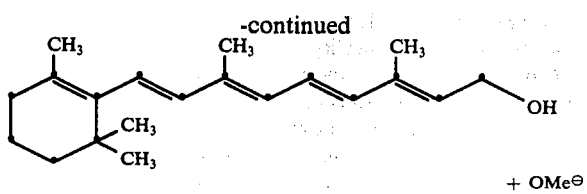

+ OMe⊖

Examples of strong basic media which may be used in the present invention are sodamide or potassium amide in liquid ammonia, with or without a co-solvent. Suitable cosolvents are ether, ethylene diamine, tetrahydrofuran (THF), pentane and amide aprotic solvents such as hexamethylphosphoramide (HMPA). Other strong basic media are lithium alkyls, e.g., methyl lithium, in ether; lithium amide in liquid ammonia and ether, or in liquid ammonia and THF; lithium diethylamide in ether or in diethylamine; and N-lithioethylenediamine in ethylene diamine. Still others are sodium or potassium-t-butoxide in aprotic solvents [e.g., dimethylformamide (DMF)]; sodium hydride in ether; methyl-sulfinylcarbanion which is the reaction product of sodium hydride in dimethylsulfoxide (DMSO). Particularly, suitable yields have been obtained employing sodamide in liquid ammonia with two co-solvents, e.g., ether and ethylene diamine. By the present invention, desired conjugated pentaenes in relatively high yields, for example 75% or higher, have been obtained.

As indicated, the treatment with a base effects an elimination of an alkanol molecule from the chain structure. This vinylogous beta-elimination of methanol, ethanol, etc., is indeed quite unexpected and surprising, since elimination of a methoxy or ethoxy group would normally be expected to occur only under acidic conditions through a carbonium ion mechanism rather than under the basic conditions of the present invention. The final polyene evolved is also quite stable in the basic medium. Thus, reverting to the use of the previous formulas, the final step in the synthesis of Vitamin A from a compound of Formula V becomes:

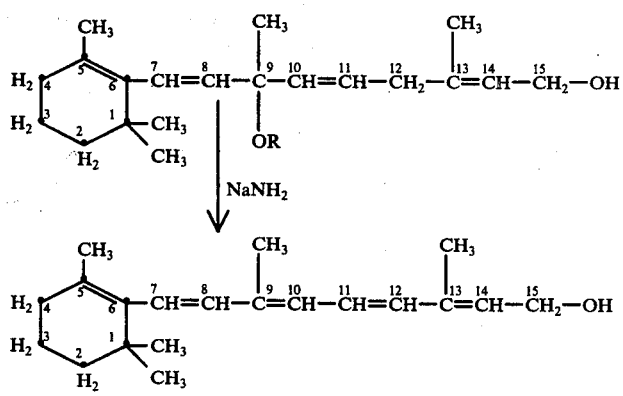

Vitamin A, Trans Form

The following examples only illustrate the invention and are not intended to limit the claims. Temperatures are on the Centigrade scale unless otherwise indicated.

EXAMPLE 1

Preparation of Ethyl Ether of Ethynyl-beta-ionol, Formula I

Beta-ionone was reacted with lithium acetylide in a known manner to produce ethynyl-beta-ionol. The eth-erification of tertiary alcohols is known to be difficult and usually results in poor yields. When an —OH group is hindered, diminishing its tendency to form alkoxide ions, additional difficulty is encountered upon attempted etherification. Unfortunately, all of these factors prevail in ethynyl-beta-ionol.

Ethynyl-beta-ionol has been successfully converted in the present invention to its lower alkyl ethers by use of alkyl sulfates, using an aprotic solvent such as dimethyl sulfoxide (DMSO) or dimethyl formamide (DMF) in a basic medium, using a base such as NaOH or $Ba(OH)_2$. The yields are excellent, running around 90 percent. In one example, the following components were used:

| | | |
|---|---|---|
| Ethynyl-beta-ionol | 65.7 g. | (0.3 mole) |
| Ethyl sulfate | 138.6 g. | (0.9 mole) |
| Sodium hydroxide (97%) pellets | 37.0 g. | (0.9 mole) |
| Dimethyl sulfoxide | 200 ml. | |

The components were placed in a one-liter, 3-neck flask equipped with a stirrer, thermometer and nitrogen inlet tube. The mixture was stirred gently with sufficient speed to move the pellets of NaOH about. Heat was slowly evolved. With the aid of only minor outside cooling, the temperature was maintained at about 35° (33° – 37°). After six hours of stirring, a second liquid phase appeared and the reaction was stopped by decanting the liquids from the unreacted NaOH. At this point, about 5 to 10 grams of unreacted NaOH remained. The flask was washed with acetone and the washings added to the reaction product. To the mixture was than added 75 ml. of concentrated aqueous $NH_4OH$ and the whole allowed to stand overnight to destroy unreacted ethyl sulfate.

The following morning the mixture was poured into two liters of brine in a large separating funnel and the precipitated oil taken up in hexane. The aqueous layer was re-extracted once with more hexane. The combined hexane extracts were washed once with water, dried over anhydrous sodium sulfate and concentrated under vacuum to an oil. This oil was then distilled through a 10 inch jacketed Vigreaux column at 0.1 mm pressure. The following fractions were obtained:

| | | |
|---|---|---|
| Fraction I | 70–71° / 0.1 mm — 2.9 g. | $n_D^{20}$ 1.4834 |
| Fraction II | 71° / 0.1 mm — 58.3 g. | $n_D^{20}$ 1.4880 |

| | | | | |
|---|---|---|---|---|
| Fraction III | 71–72° / 0.1 mm — 7.6 g. | $n_D^{20}$ | 1.4898 |
| | Distillation residue — 4.1 grams. | | |

The infrared spectrum analysis of the main fraction II showed no free hydroxyl group. The ultraviolet spectrum analysis showed only a single maximum $\lambda_m$ 236 m$\mu$, characteristic of the beta-ionol chromophore. However, some ethynyl-beta-ionol may be present in the crude product and, if so, may be removed by the procedure of Example 2.

EXAMPLE 2

Preparation of Ethyl Ether of Ethynyl-beta-ionol, Formula I

The reaction mixture comprised:

| | |
|---|---|
| Ethynyl-beta-ionol | 130.5 g. |
| Ethyl sulfate | 278 g. |
| Hydrated barium hydroxide | 222 g. |
| Dimethyl sulfoxide | 400 g. |

The mixture was maintained at 24° to 27° for about 11 hours. After percolating the worked up reaction mixture through a column of 650 grams of alumina and washing with pentane, a product of 125.7 grams was obtained of the ethyl ether of ethynyl-beta ionol. The yield had a boiling point of 74° at 0.18 mm. of mercury, $n_D^{24}$ 1.4842.

The total distillate consisted of a single fraction. It was free of hydroxyl as evidenced by no hydroxyl band in its infrared curve. The distillate had a strong acetylene hydrogen band at 3.0–3.1 m$\mu$, and the ether doublet at 9.12 and 9.34 m$\mu$. The ultraviolet curve showed a peak at 236 m$\mu$ showing the beta-ionyl group to be intact.

On elution of the column of alumina with diethyl ether, a yield was obtained of 9.2 grams of unchanged ethynyl-beta-ionol.

EXAMPLE 3

Preparation of Methyl Ether of Ethynyl-beta-ionol, Formula I

| | | |
|---|---|---|
| Ethynyl-beta-ionol | 68.1 g. | (0.315 mole) |
| Methyl sulfate | 119 g. | (0.945 mole) |
| Hydrated barium hydroxide | 96.4 g. | (0.506 mole) |
| Dimethyl formamide | 215 ml. | |

The ionol, barium hydroxide and dimethyl formamide are placed in a one liter, three-necked flask equipped with a mechanical stirrer, thermometer and nitrogen inlet tube. Under steady stirring, the methyl sulfate is added dropwise at 10°. Reaction is very slow at this temperature. On raising the temperature to 17°, heat begins to evolve. By external cooling, the temperature was maintained at 20°–21°. Within 1.5 to 2 hours most of the barium hydroxide had dissolved and the exothermic effect was gone. Stirring was continued at 19° to 20° for four hours.

The reaction mixture was then poured into two liters of 5 percent aqueous ammonium hydroxide and 500 ml. of hexane. A precipitate of barium salts made separation difficult, and the precipitate was removed by filtration. The hexane layer was removed, dried over anhydrous sodium sulfate, and concentrated under vacuum.

The residual oil was distilled, and these fractions were obtained:

| | | | |
|---|---|---|---|
| Fraction I | 59° / 0.07 mm — 0.2 g. | $n_D^{20}$ | 1.4960 |
| Fraction II | 59–60° / 0.07 mm — 61.4 g. | $n_D^{20}$ | 1.4971 |
| Fraction III | 59–60° / 0.07 mm — 1.8 g. | $n_D^{20}$ | 1.5015 |

The infrared spectrum of fraction II showed some free hydroxyl present, presumably from unreacted ethynyl ionol.

EXAMPLE 4

Separation of the ether of either Examples 1 or 2, was also obtained by percolating a pentane or hexane solution of the reaction product through a column having granular alumina (Alcoa F-20) in an amount of 4 to 5 times the weight of the crude product. Unreacted ethynyl-beta-ionol is retained on the column while desired ether passes through on washing with pentane or hexane. Unchanged ethynyl-beta-ionol was than recovered by eluting the column of alumina with diethyl ether.

EXAMPLE 5

Coupling Reaction, Preparation of Formula III

Alkylation of a compound of Formula I having a terminal acetylene group with a chloro-ester via the acetylenic Grignard derivative is impractical, since the Grignard reagent reacts more readily with the ester group, such as contained in the chloro-acetate. In the present invention, the acetylene moiety is first converted to the copper derivative. Such compounds are inert toward esters but can displace the halide from organic halides. In this example, the following components were used:

| | |
|---|---|
| Ethynyl-beta-ionol ethyl ether | 12.3 g. (0.05 mole) |
| Magnesium | 1.4 g. |
| Ethyl bromide | 7.5 g. |
| Tetrahydrofuran | 50 ml. |
| Cuprous chloride | 6.6 g. |
| Hexamethyl phosphoric tri-amide | 100 ml. |
| 1-chloro-4-acetoxy-2-methyl-2-butene | 12.5 g. |

In a three-necked flask fitted with a mechanical stirrer, condenser, thermometer and nitrogen inlet tube, the ethyl magnesium bromide was prepared in 40 milliliters of the tetrahydrofuran in a conventional manner. The acetylenic ether was then added at room temperature using the last 10 milliliters of tetrahydrofuran. Evolution of ethane started at once, and the mixture was stirred and heated for two hours when gas evolution ceased. To the solution of acetylenyl Grignard reagent thus formed, the hexamethyl phosphoric tri-amide was added at room temperature.

The reaction flask was then flushed with nitrogen and under a positive pressure of nitrogen, the cuprous chloride was added at room temperature. It dissolved immediately. The mixture was then stirred at 65° for 30 minutes and the chloroacetoxy methylbutene added at once. The mixture was then stirred at 83° to 92° for six hours under nitrogen.

The reaction was quenched by pouring the mixture into one liter of an aqueous solution of 10 percent NH$_4$Cl and 5 percent NH$_4$OH, layered with 300 ml. of pentane. After thorough mixing, the pentane layer was separated, dried over sodium sulfate and concentrated under vacuum. To remove unreacted chloroisopentenyl acetate, 50 ml. of diethyl amine were added and the solution allowed to stand at room temperature overnight.

The following morning a precipitate of Et$_2$NH.HCl was present. The mixture was washed twice with brine, five times with 15 percent acetic acid, then with water, and finally with NaHCO$_3$ solution. After drying with sodium sulfate, the product was concentrated under vacuum. Unchanged starting ether was removed by treatment with neutral alumina (Alcoa F-20).

The infrared spectrum of the product obtained showed the presence of the acetate group and the ether group. Its ultraviolet spectrum showed a single maximum at 236 m$\mu$, characteristic of the beta-ionol group diene.

EXAMPLE 6

Alternatively in Example 5, should the product show the presence of unreacted chloride after the diethylamine treatment, the chloride should be removed as follows prior to distillation to avoid decomposition.

The reaction product at the stage indicated was passed through a column of neutral alumina without making any attempt at chromatographic fractionation. The chloride was removed and the product recovered by washing the column of alumina with diethyl ether. The wash product was then distilled under high vacuum and collected at 98° to 105° at 0.001 mm. mercury, $n_D^{22}$ 1.4950. This product was the acetate form of Formula III. The infrared spectrum showed allylic ester bands at 5.75 $\mu$, 8.16 $\mu$, and 9.77 $\mu$. The ether doublet was at 9.1 $\mu$ and 9.21 $\mu$. The ultraviolet showed the betaionyl chromophore at $\lambda_m$ 236 m$\mu$.

EXAMPLE 7

This example illustrates a further technique for treating the crude reaction product of Example 5 obtained from the coupling reaction. Such reaction product was concentrated under vacuum and dissolved in 2 percent methanolic sodium hydroxide. The solution was then allowed to stand at room temperature under a blanket of nitrogen for 12 hours. The unreacted chloride present and the ester groups on the coupling product were thereby hydrolyzed.

The mixture was next quenched with water and the resulting precipitated oil taken up in pentane, dried with sodium sulfate, and distilled under vacuum. The product was collected at 100° to 110° at 0.001 mm of mercury, $n_D^{24.5}$ 1.5060. The infrared spectrum showed a prominent hydroxyl band at 2.9 $\mu$ and no ester bands. The ultraviolet spectrum showed the typical beta-ionyl chromophore, $\lambda_m$ 236 m$\mu$. The resulting product corresponded to a compound of Formula III in which R$^1$ was hydrogen.

EXAMPLE 8

Semi-Hydrogenation of Coupling Product, Preparation of Formula IV

A solution of 2.6 grams of an acetate compound of Formula III in 50 ml. of hexane was stirred under hydrogen with 1.56 grams of lindlar catalyst (5 percent Pd on CaCO$_3$) at 22°. Absorption of hydrogen ran at about 6.0 ml./min. At the theoretical end-point, 176 milliliters of hydrogen at 22°, the rate of absorption had fallen to 0.8 ml./min. The catalyst was filtered off and the hexane removed under vacuum. The product was a light yellow oil; the yield was 2.52 g.

The infrared spectrum of this oil showed the presence of the acetate and ether groups, indicating no hydrogenolysis had occurred. The ultraviolet spectrum of the oil showed a single maximum at 236 m$\mu$, showing the betaionyl diene still intact.

EXAMPLE 9

Hydrolysis of Semi-Hydrogenated Coupling Product, Preparation of Formula V

The semi-hydrogenated, acetate coupled product of Example 8 was dissolved in a one percent solution of sodium hydroxide in methyl alcohol. The solution was allowed to stand about 12 hours at room temperature under a blanket of nitrogen. The hydrolysis was complete as shown by the total absence of ester bands in an infrared analysis.

EXAMPLE 10

De-esthanolation of the Semi-Hydrogenated, Hydrolyzed Coupling Product, Preparation of Vitamin A The product of Example 9, was placed in anhydrous ether solution and the mixture added to a suspension of freshly prepared sodamide in liquid ammonia in a weight ratio of about 2.28 product:25 ether:1.36 sodamide:100 ammonia. At minus 40° no reaction appeared to take place other than the formation of the alkoxide of the starting material. On raising the temperature to minus 30°, the reaction mixture turned a deep opaque purple which remained for the duration of the run. After two hours the reaction mixture was quenched with ammonium chloride.

Separation of Vitamin A from the product obtained was achieved by acetylating the total reaction product using pyridine-acetic anhydride at room temperature and chromatographing on alumina neutralized with acetic acid. A fairly clean separation was achieved. The Vitamin A acetate fraction was sufficiently pure to become crystallized from pentane at minus 15° when seeded with a pure Vitamin A acetate crystal.

As determined chromatographically, the results of this example were as follows in weight percent.

| | |
|---|---|
| Vitamin A (as acetate) | 62% |
| Ethylenic coupling product of | |
| Example 4 | 35% |
| Unknown hydrocarbons | about 3% |

When the Vitamin A acetate was converted to the alcohol form of Vitamin A, the final product showed the characteristic infrared and ultraviolet absorption curves for Vitamin A. Similar results were obtained using as cosolvents (with the liquid ammonia) ethylene diamine and ether;pentane; tetrahydrofuran; diethylamine and hexamethylphosphoramide.

By the present process the vioissitudes and uncertainties of acid-promoted carbonium ion reactions leading to isomeric mixtures are avoided. In addition the Vitamin A evolves into a basic medium where its stability is much enhanced over that in an acid medium.

I claim:

1. A process for forming Vitamin A which includes the steps of;
   pre-preparation of a class of compounds having the general formula:

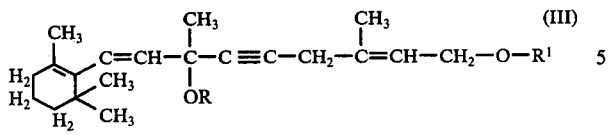 (III)

in which R is a lower alkyl, lower alkenyl, phenyl or aralkyl and R¹ is hydrogen or

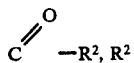

being lower alkyl, phenyl, or aralkyl, said pre-preparation comprising coupling the acetylenyl group of a compound having the general formula:

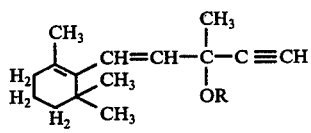 (I)

in which R has the same meaning with a reactant having the general formula:

$$R^3-CH_2-\overset{\underset{\displaystyle CH_3}{|}}{C}=CH-CH_2-O-R^1 \quad (II)$$

in which $R^3$ is halogen, by first forming the cuprous acetylenyl derivative of a compound of formula I and then reacting said derivative with a compound of the formula II;

semi-hydrogenating the acetylenic bond of the compound of formula III to form a class of compounds having the general formula:

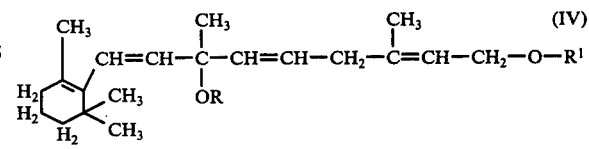 (IV)

in which R and R¹ have the same meaning as above; and subjecting the compound of formula IV to the presence of a sufficiently strong basic medium to effect 1,4 elimination of ROH therefrom, formation of an additional double bond and conjugation of all five double bonds in the molecule in order to form Vitamin A.

2. The process of claim 1 wherein said basic medium is selected from the group consisting of sodamide or potassium amide in liquid ammonia, with or without a co-solvent, suitable co-solvents being ether, ethylene diamine, tetrahydrofuran, pentane, amide aprotic solvents such as hexamethylphosphoramide, and combinations thereof.

* * * * *

UNITED STATES PATENT AND TRADEMARK OFFICE
CERTIFICATE OF CORRECTION

PATENT NO. : 4,064,183
DATED : December 20, 1977
INVENTOR(S) : William Oroshnik

It is certified that error appears in the above-identified patent and that said Letters Patent are hereby corrected as shown below:

Col. 3, line 19, change "cia" to --cis--; Col. 6, line 2, change "acryl" to --acyl--; line 65, in the formulation the portion reading

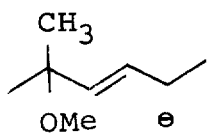   should read   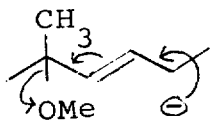

Col. 8, line 33, change "than" to --then--. Col. 12, line 19, change "De-esthanolation" to --De-ethanolation--; line 58, change "vioissitudes" to --vicissitudes--.

Signed and Sealed this

Sixteenth Day of May 1978

[SEAL]

Attest:

RUTH C. MASON
Attesting Officer

LUTRELLE F. PARKER
Acting Commissioner of Patents and Trademarks